United States Patent [19]
Mirza

[11] Patent Number: 5,578,051
[45] Date of Patent: *Nov. 26, 1996

[54] ENDOSCOPIC SURGICAL PROCEDURE AND INSTRUMENT FOR IMPLEMENTATION THEREOF

[75] Inventor: M. Ather Mirza, St. James, N.Y.

[73] Assignee: Theodor Esser and Eugene T. King, East Northport, N.Y.

[ * ] Notice: The term of this patent shall not extend beyond the expiration date of Pat. No. 5,366,465.

[21] Appl. No.: 314,330

[22] Filed: Sep. 28, 1994

Related U.S. Application Data

[63] Continuation-in-part of Ser. No. 16,048, Feb. 10, 1993, Pat. No. 5,366,465, which is a continuation of Ser. No. 986,523, Dec. 7, 1992, abandoned.

[51] Int. Cl.$^6$ ..................... A61B 17/32
[52] U.S. Cl. ............ 606/170; 600/104; 606/172; 128/898
[58] Field of Search .................. 606/159, 170, 606/172; 604/22; 128/898; 600/104–107, 109, 113, 117, 118, 135, 136, 138, 139, 153, 160, 166, 167, 184, 199–201, 204, 219

[56] References Cited

U.S. PATENT DOCUMENTS

| | | |
|---|---|---|
| 1,880,551 | 10/1932 | Wappler . |
| 4,497,320 | 2/1985 | Nicholson et al. . |
| 4,499,899 | 2/1985 | Lyons, III . |
| 4,512,344 | 4/1985 | Barber . |
| 4,610,242 | 9/1986 | Santangelo et al. . |
| 4,723,546 | 2/1988 | Zagorski . |
| 4,766,896 | 8/1988 | Pao . |
| 4,819,620 | 4/1989 | Okutsu . |
| 4,834,729 | 5/1989 | Sjostrom . |
| 4,877,026 | 10/1989 | de Laforcade . |
| 4,923,441 | 5/1990 | Shuler .................... 604/22 |
| 4,962,770 | 10/1990 | Agee et al. . |
| 4,963,147 | 10/1990 | Agee et al. ............. 606/170 |
| 4,969,450 | 11/1990 | Chinnock et al. . |
| 4,983,179 | 1/1991 | Sjostrom ................ 606/180 |
| 4,986,825 | 1/1991 | Bays et al. ............. 604/22 |
| 5,007,917 | 4/1991 | Evans ..................... 606/170 |
| 5,029,573 | 7/1991 | Chow . |
| 5,061,238 | 10/1991 | Shuler .................... 604/22 |
| 5,089,000 | 2/1992 | Agee et al. ............. 606/170 |
| 5,106,364 | 4/1992 | Hayafuji et al. ....... 604/22 |
| 5,323,765 | 6/1994 | Brown . |
| 5,366,465 | 11/1994 | Mirza ..................... 606/170 |

FOREIGN PATENT DOCUMENTS 2601802  7/1977  Germany .

Primary Examiner—John D. Yasko
Assistant Examiner—Ronald K. Stright, Jr.
Attorney, Agent, or Firm—Scully, Scott, Murphy & Presser

[57] ABSTRACT

Method of implementing endoscopic surgical procedures on a patient, and more particularly, a novel and unique technique of performing uniportal surgical entries. Moreover, also disclosed is a unique endoscopic surgical instrument including a unique cutting device adapted to be employed in the implementation of the foregoing methods of endoscopically effecting the uniportal carpal tunnel release. This surgical procedure only requires the formation of a single and relatively small entry portal or incision in the patient, resulting in minimum discomfort.

16 Claims, 3 Drawing Sheets

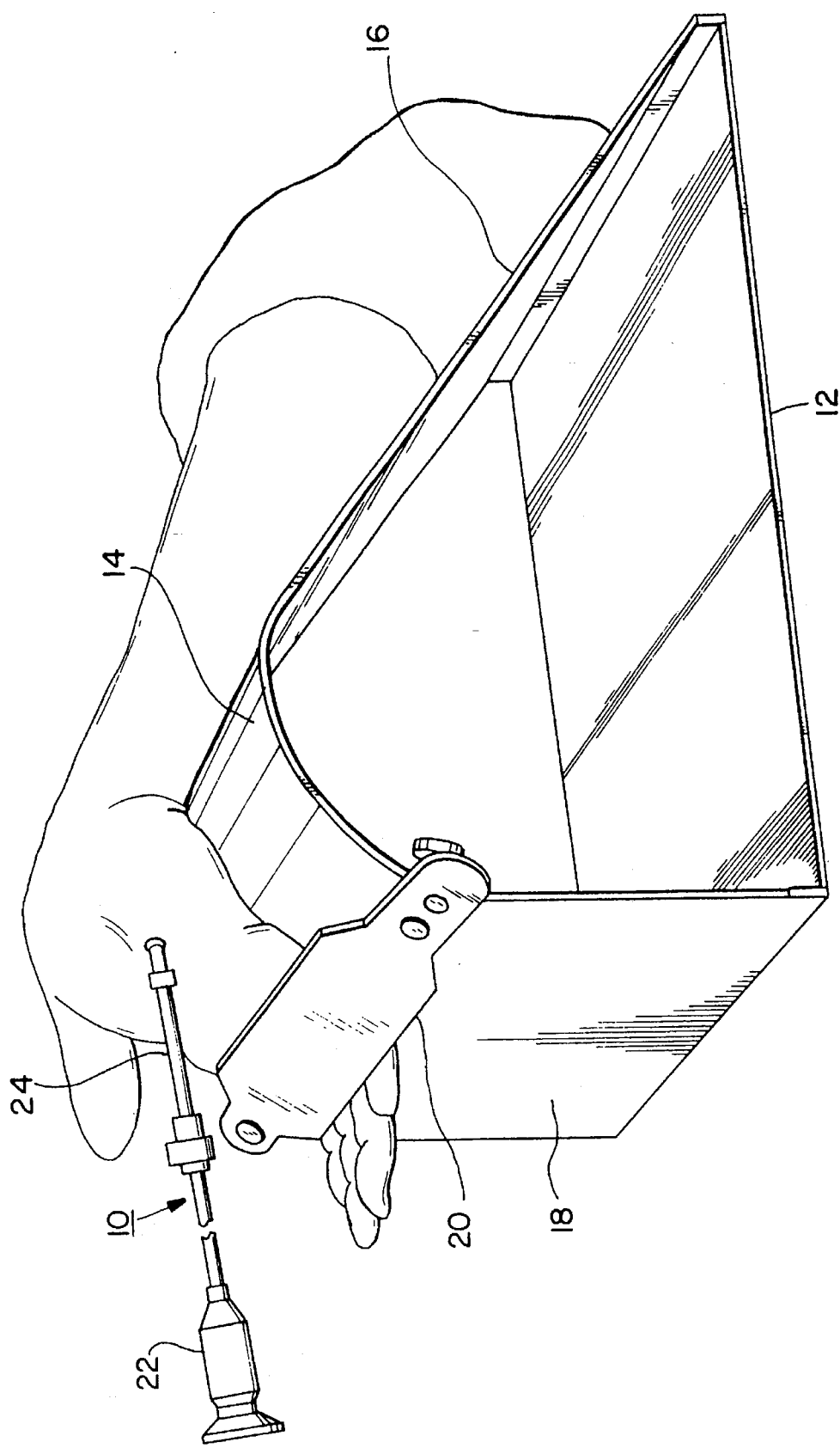

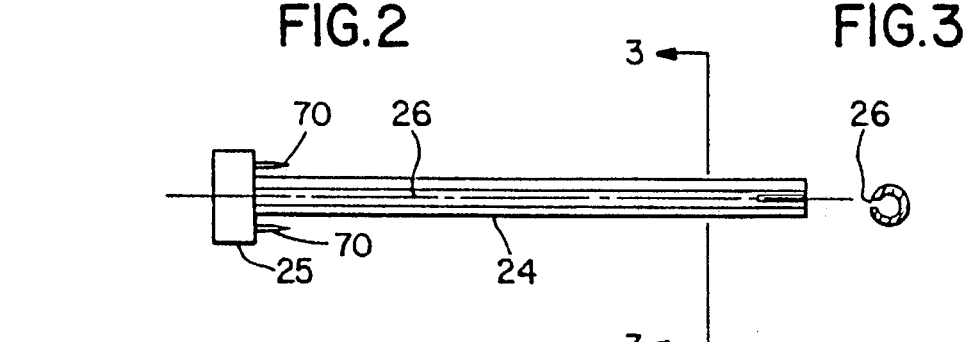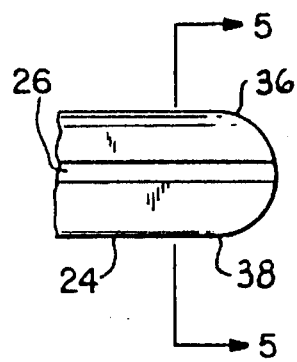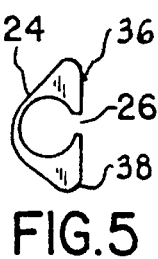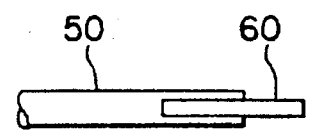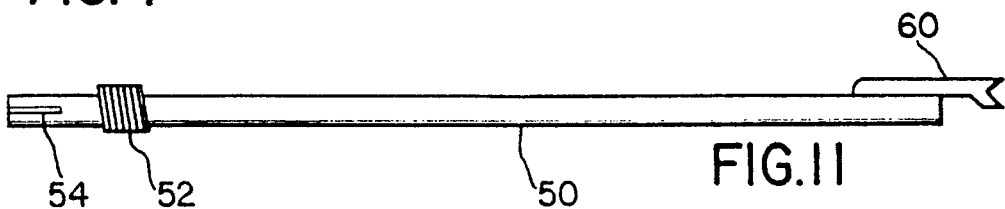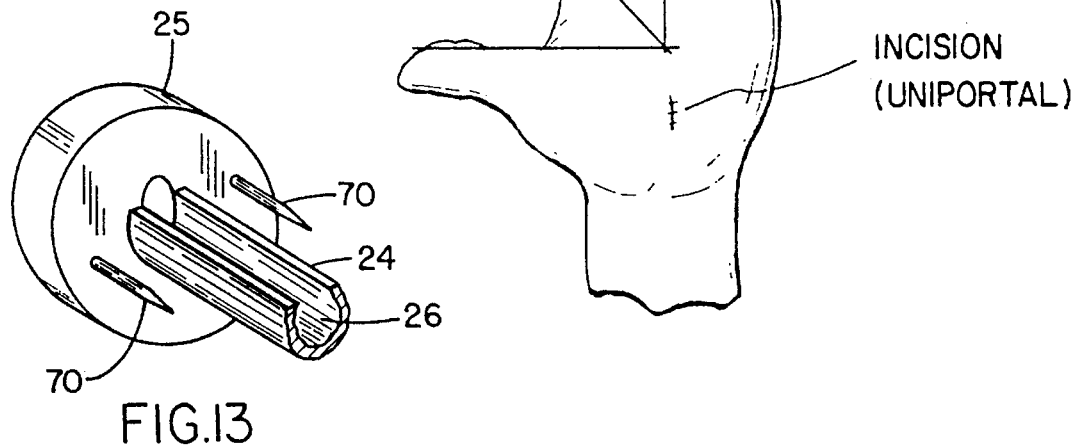

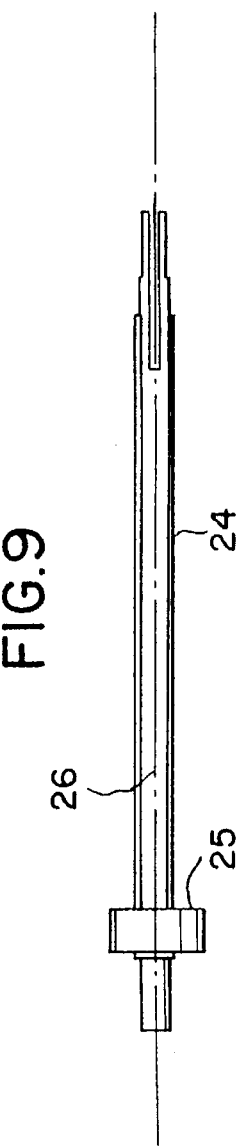
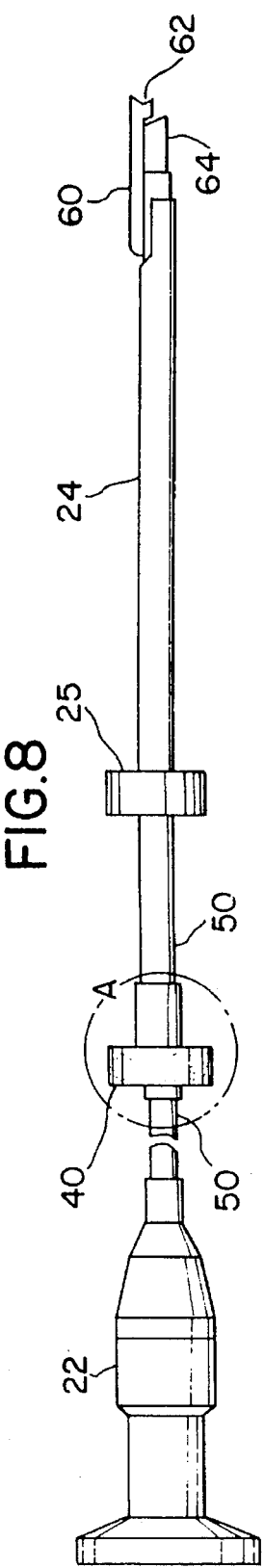
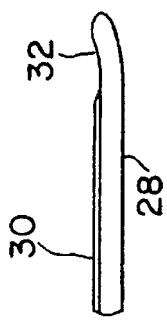
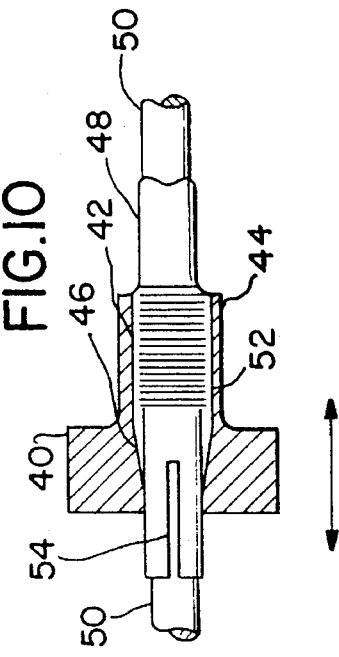

ENDOSCOPIC SURGICAL PROCEDURE AND INSTRUMENT FOR IMPLEMENTATION THEREOF

CROSS-REFERENCE TO RELATED APPLICATIONS

This application is a continuation-in-part application of Ser. No. 08/016,048, filed Feb. 10, 1993, new U.S. Pat. No. 5,366,465, which is a continuation application of Ser. No. 07/986,523, filed Dec. 7, 1992, now abandoned.

BACKGROUND OF THE INVENTION

1. Field of the Invention

The present invention relates to methods of implementing an endoscopic surgical procedure on a patient, and more particularly, is directed to a novel and unique technique of performing endoscopic surgical procedures including such as uniportal plantar fascia release, lateral release for patella realignment, release of the posterior and other compartments of the leg, forearm fascial release for fascial compartment syndrome, and uniportal palmar subligmentous endoscopic carpal tunnel release. Moreover, the invention is also directed to the provision of a unique endoscopic surgical instrument adapted to be employed in the implementation of the foregoing method of endoscopically effecting the above-referenced surgical procedures.

In particular, although initially directed to a method of implementing an endoscopic surgical procedure to effect carpal tunnel release, as mentioned, numerous other surgical procedures may be readily implemented employing the inventive instrument as described herein.

Basically, initially the method and instrument were directed to the implementation of endoscopic carpal tunnel release, as set forth in parent application Ser. No. 08/016,048, now U.S. Pat. No. 5,366,465.

Carpal tunnel syndrome is a numbness in the thumb, index, middle and ring fingers resulting from pressure being exerted on the median nerve inside the carpal tunnel, interfering with the function of such median nerve. This may readily manifest itself as a pain radiating as far as the shoulders and neck of the patient, resulting in impaired grasping ability by the hand and loss of sleep. This physical phenomenon is the result of repetitive work and motions being carried out with the hand over lengthy periods of time, and is experienced by more ever younger people.

In essence, the carpal tunnel is formed by an arch of the eight wrist bones, spanned on its palmar surface by the transverse carpal ligament, the flexor retinaculum. The carpal tunnel functions as a large mechanical pulley to provide the appropriate moment arms for the digital flexor tendons as they pass through the tunnel. The tendons can then transmit force out into the fingers and impart only an appropriate amount of tension to develop torque at the level of the wrist.

Within the carpal tunnel, these tendons are lubricated and nourished by two synovial membranes—the radial and the ulnar bursa. The median nerve also shares the carpal tunnel, then branches out to provide sensory innervation to the palmar surfaces of the thumb, index, long and a portion of the ring finger. In addition, a small motor branch of the median nerve supplies the thenar muscles, which are responsible for lifting the thumb into opposition with the fingers.

Currently, a considerable array of methods or surgical techniques, and suitable therewith correlated surgical instruments, are being employed for purposes of implementing surgical procedures in effectuating carpal tunnel release in patients, and are generally designed for particular and highly specialized applications in this medical technology.

The customary procedure in implementing carpal tunnel release has heretofore been the forming of a lengthy incision, up to 8 cm in length across the palm from the wrist to the middle thereof, resulting in an unsightly scar, requiring division of all anatomical structures between the skin and the flexor retinaculum; i.e. the transverse carpal ligament. This created the potential for inadvertently cutting or injuring the palmar cutaneous nerve. Moreover, the patent normally encountered significant postoperative pain and discomfort, weakness of grip and pinch strength because of pillar infraction and the excessively lengthy extent of the incision. Such open surgery not only normally left the patient with a cosmetically unsightly scar extending from the wrist to the center of the palm, as mentioned hereinbefore, but also necessitated a lengthy and painful convalescence for the patient, whereby this convalescent period frequently caused the hand to be incapable of any-significant physical work or manipulation for many weeks and even months, thereby effectively rendering the patient incapable of carrying out any meaningful work with the operated on hand and resulting in considerable financial losses being sustained by the patient.

Among more recent developments and advances in such surgical procedures, arthroscopic surgery employing the use of endoscopic devices has found widespread application, among others in connection with carpal tunnel release, in that in comparison with earlier customary surgical methods, any incisions necessary for such endoscopic/arthroscopic surgical procedures have been considerably reduced in size, thereby alleviating potential postoperative complications and pain encountered by the patient, while reducing any scarring to cosmetically desirable levels. Among various types of surgical procedures, techniques involving approaches by means of arthroscopic and endoscopic systems to carpal tunnel surgery have been acknowledged as being superior in providing significant advances over earlier so-called open surgical procedures necessitating large incisions. Such endoscopic surgical procedures have found widespread acceptance in effectuating carpal tunnel release for the purpose of alleviating the symptoms in a patient caused by carpal tunnel syndrome, also referred to as tardy median nerve palsy, normally caused by the compression of the median nerve within the carpal tunnel.

More recently, consideration has been given towards extending the scope of the endoscopic surgical procedure to other aspects such as plantar fascia release associated with heel spur syndrome in which a patient encounters severe pain at the bottom of the foot. This aspect, which is caused by the dense fibrous band of tissue which is known as the plantar fascia, is that a disorder of the foot, such as a structural misalignment, can cause an inflammation and result in intense pain in the foot. Although in many instances therapy may remedy the problems which are encountered, at times surgery is necessary in order to alleviate the problems.

These more recent endoscopic surgical approaches to remedying varying types of surgical problems afforded desirable alternatives to such earlier open surgical procedures, and especially when applied to effectuating carpal tunnel release, have found widespread favor with surgeons and patients in comparison with the earlier surgical methods which primarily constituted complex open surgical procedures, and which involved lengthy and painful postoperative convalescent periods.

2. Discussion of the Prior Art

Among numerous publications which describe recent advances in endoscopic surgical methods and instruments employed in connection therewith, particularly such as may be employable for carpal tunnel release procedures, there may be found the Agee carpal tunnel release system as disclosed in Agee, et al. U.S. Pat. Nos. 4,963,147 and 5,089,000, both of which disclose endoscopic surgical instruments and surgical procedures implemented therewith, which when applied to carpal tunnel release through an effective severing of the flexor retinaculum, or transverse carpal ligament, are adapted to provide relief to the patient. However, the instrument and methods developed by Agee, et al. as described in those publications, although superior to open surgery, inhibit readily unobstructed visualization of the surgical site during the sequence of severing the flexor retinaculum and do not provide adequate control in the manipulation of the instrument so as to reduce the inherent danger of damage to surrounding nerves and tissue to an acceptable minimum, and additionally necessitate the forming of two entry portals or incisions in the wrist and hand. Moreover, the endoscopic instruments developed in Agee, et al. are relatively cumbersome and expensive, requiring the surgeon to always use both of his hands, and necessitate the use of a swivel cutting blade construction operable independently of a viewing scope, which does not always provide the appropriate visualization during cutting of the flexor retinaculum so as to potentially present the danger of causing damage to adjacent or contiguously located tissue or nerves relative to the operating site, which could lead to serious and possibly permanent injury to the patient.

Another surgical system and instrument providing for an advanced technique over Agee, et al., which is particularly adapted for carpal tunnel release through the intermediary of an endoscopic surgical procedure is disclosed in Chow U.S. Pat. No. 5,029,573. However, in that instance, although setting forth a considerable advance over the methodology disclosed in the Agee, et al. U.S. patents, the surgical procedure employed by Chow requires the formation of two entry and exit portals or incisions, one in the wrist area and one in the palm, and the passage of an endoscopic medical instrument, such as an obturator through a considerable length beneath the subcutaneous areas of the palm of the patient. Again, the necessity for two widely separated incisions or entry portals, and the requirement for inserting a scope from one end of the instrument from one portal and with the instrument extending outwardly from the other portal or incision, while surgically severing or cutting through the flexor retinaculum or transverse carpal ligament from the other portal or incision, engenders a considerable obstruction toward a clear nonproblematic visualization of the operating site during the severing of the transverse carpal ligament and, once again, raises the specter of a potential risk of causing injury to tissue and nerves adjacent the operating site, especially such as to the median nerve, which could lead to serious permanent injury to a patient and possibly require additional corrective surgery necessitating subjecting the entire surgical or operating site to open surgery. Moreover, Agee, et al. and Chow require the surgeon to simultaneously employ both hands during the surgical procedures, thus necessitating the utilization of an unusually high degree of dexterity in manipulating the various components of the endoscopic surgical instruments.

Another method of endoscopic surgery and instrument for implementing surgery, particularly for the release of the carpal tunnel, are disclosed in Brown U.S. Pat. No. 5,323,765. Although Brown directs the endoscopic surgery towards alleviating the syndrome encountered with the carpal tunnel, as in the previously discussed publications, two separate incisions are required. Moreover, although Brown also briefly mentions the application of the surgery and instrument or apparatus to the treatment of the foot, particularly the plantar fascia, again there is no detailed explanation provided as to the method in which this is accomplished, and apparently this would also necessitate providing a plurality of separate incisions to implement the surgery.

SUMMARY OF THE INVENTION

The foregoing limitations and potential drawbacks which are encountered in the prior art publications are clearly and unambiguously obviated and improved upon through the inventive and novel method of implementing endoscopic surgical procedures, and the unique and inventive endoscopic surgical instrument developed for accomplishing this purpose, which has proven itself to be especially suited for the effectuation of a carpal tunnel release; in essence, the severing of the flexor retinaculum or transverse carpal ligament through an endoscopic surgical procedure in which there is effected, by means of a uniportal or single incision, a palmar subligmentous endoscopic carpal tunnel release technique. This surgical procedure only requires the formation of a single and relatively small entry portal or incision in the palm proximate the distal side of the flexor retinaculum, thereby reducing any postoperative symptoms of the patient with only a cosmetically appealing scar formed on the palm, while eliminating the need for a second portal or incision proximate the wrist of the patient; and concurrently avoiding injury to the palmar arch and branches of the median nerve. Moreover, the endoscopic instrument employed in implementing the inventive method utilizes a unique cutting device which is mounted on a scope insertable through a cannula which has been initially inserted to extend beneath the flexor retinaculum from the distal side of the flexor retinaculum or transverse carpal ligament, upon the formation of a passage beneath the flexor retinaculum, after hyperextending of the hand, by the preceding insertion and manipulation of a curved dissector. Thereafter, the dissector is removed and the cannula and an obturator which is contained therein are inserted through the incision into the previously formed passage beneath the flexor retinaculum. The cannula of the surgical instrument has the obturator withdrawn therefrom, and in place of the latter, a scope is inserted into the cannula which enables unhindered and unobstructed visualization of the operating site and of the flexor retinaculum.

The scope is then withdrawn from the cannula, and the same scope or another scope with a cutting blade mounted at the leading end thereof inserted into and advanced through the cannula towards the flexor retinaculum. Severing of the latter is then effected by the cutting blade while affording an unhindered view of the operating site through the scope, thereby resultingly dramatically reducing or even completely eliminating the risk of any injury being sustained by tissue and nerves in the vicinity of the operating site; for example, such as the median nerve. This particular unhindered visualization of the operating site also enables the surgeon to exercise an improved degree of control over the possibly single-handed manipulation of the endoscopic instrument and cutting blade.

Although described hereinabove with regard to the effectuation of a carpal tunnel release, the inventive uniportal endoscopic surgical methods and instrument may be also be readily applied to other surgical procedures; for example, such as uniportal plantar fascia release, lateral release for patella realignment, release of the posterior and other compartments of the leg, and forearm fascia release for fascial compartment syndrome.

Pursuant to a feature of the invention, the guiding member or cannula of the endoscopic instrument, and which contains the obturator which is initially employed to be advanced beneath the flexor retinaculum or transverse carpal ligament subsequent to withdrawal of the curved dissector, is provided with lateral or sideways wing-like or flange-like protrusions of curvilinear configurations which, in conjunction with an upwardly curving tip of the obturator projecting forwardly of the leading end of the cannula, is adapted to displace any tissue, or such as the media nerve, out of the path of the obturator and cannula as is being advanced; in effect, through essentially a sideways or lateral "shoving" action, thereby preventing any potential damage to such displaced tissue and nerve during the subsequent cutting procedure by maintaining such tissue well out of the way. Moreover, the leading tip of the obturator by being curved slightly upwardly towards the lower surface of the flexor retinaculum is also adapted to remove or dislocate any possible tissue or fascia located close to the surface of the flexor retinaculum and to ensure that the cannula and, resultingly, the subsequently inserted cutting blade are located as closely as possible to the flexor retinaculum.

The foregoing inventive concept ensures the provision of simple and extremely efficient endoscopic surgical procedures which are particularly adapted, in conjunction with the use of the novel endoscopic instrument, for the implementation of a carpal tunnel release through the severing of the flexor retinaculum while producing minimal or no postoperative pain and discomfort in the patient, with a shortened convalescent period and with the formation only of a small cosmetically attractive scar on the palm of the patient's hand. This aspect is also readily applicable to the endoscopic surgical procedures described with regard to the uniportal plantar,fascia release, lateral release for patella realignment, release of the posterior and other compartments of the leg, and the forearm fascial release for fascial compartment syndrome as described hereinbelow.

Accordingly, it is a primary object of the present invention to provide a novel and unique method of implementing an endoscopic surgical procedure through a uniportal entry to an operating site by a novel endoscopic surgical instrument.

The present invention has as a further object to provide an endoscopic surgical instrument with a novel scope-mounted cutting or blade element for implementing the endoscopic surgical procedure pursuant to the invention.

Still another object of the present invention is to provide an endoscopic surgical instrument of the type described, in which a scope which is adapted to be advanced through a cannula located beneath the flexor retinaculum has a cutting device mounted thereon to enable severing of the flexor retinaculum while being able to afford the surgeon an unobstructed visualization of the operating site, and avoiding damage or injury to the palmar arch and branches of the median nerve.

Yet another object of the present invention is to provide a novel uniportal endoscopic surgical method which may be readily applied to various types of surgical procedures in addition to the treatment of carpal tunnel syndrome.

BRIEF DESCRIPTION OF THE DRAWINGS

Reference may now be had to the following detailed description of preferred embodiments of the endoscopic surgical instrument constructed pursuant to the invention, and to a surgical procedure for the effectuation of carpal ligament or tunnel release on a patient by a transverse severing of the flexor retinaculum, taken in conjunction with the accompanying drawings; in which:

FIG. 1 illustrates a generally perspective view of the hand of the patient in a hyperextended position during a surgical procedure for effecting carpal ligament release, utilizing the endoscopic surgical instrument pursuant to the invention;

FIG. 2 illustrates a longitudinal top view of a slotted cannula of the endoscopic surgical instrument pursuant to the invention;

FIG. 3 illustrates a sectional view taken along line 3—3 in FIG. 2;

FIG. 4 illustrates a top view of the leading end portion of a modified slotted cannula;

FIG. 5 illustrates a sectional view taken along line 5—5 in FIG. 4;

FIG. 6 illustrates a longitudinal side view of the leading end of an obturator adapted to be inserted into the slotted cannula of FIGS. 2 or 4;

FIG. 7 illustrates a top view of the leading end of the obturator;

FIG. 8 illustrates a longitudinal side view of the endoscopic instrument, showing the scope and cutting device mounted on the latter inserted into the slotted cannula;

FIG. 9 illustrates a top view of the leading section of the endoscopic instrument shown in FIG. 8;

FIG. 10 illustrates, on a somewhat enlarged scale, a sectional view of the encircled portion 'A' of the instrument of FIG. 8;

FIG. 11 illustrates a longitudinal side view of a scope and cutting device or blade mounted theron prior to the insertion thereof into the slotted cannula;

FIG. 12 illustrates a top view of the leading end portion of the scope and cutting device of FIG. 11;

FIG. 13 illustrates a fragmentary perspective view, shown on an enlarged scale, of a portion of the slotted cannula showing the locating pins; and FIG. 14 illustrates the palm portion of the hand of a patient showing the surgical markings applied thereto prior to implementing the incision for the endoscopic carpal tunnel releasing surgery.

DETAILED DESCRIPTION

Reverting now in more specific detail to the description of the invention as represented by drawing FIGS. 1 through 12, FIG. 1 of the drawings illustrates an endoscopic system 10 employed for the procedure of effectuating the surgical release of a transverse carpal ligament; in essence, the severing of a flexor retinaculum in order to alleviate the symptoms and debilitating effects of carpal tunnel syndrome.

In this instance, the hand of a patient with the endoscopic system 10 is supported on a hand rest 12, which is in the form of a bolster having a curved upper surface 14 between an inclined or sloping surface 16 enabling the lower arm portion of a patient to be supported thereon, and a vertically depending front surface 18 with a strap 20 attached thereto for maintaining the hand of the patient in a hyperextended position in readiness for the endoscopic surgical procedure.

As shown in FIG. 1 of the drawings, the endoscopic instrument 10 which is to be utilized for effectuating the carpal ligament release; in effect, the severing or transverse cutting through of the flexor retinaculum, is shown in the operative position thereof inserted through an incision into the hand of a patient; with the surgical procedure being set forth in more specific detail hereinbelow.

Referring to FIGS. 1 through 13 of the drawings, and particularly FIGS. 2 through 10, the endoscopic surgical instrument 10 comprises an arthroscope 22 which includes a cannula 24 having a through extending longitudinal slot 26 formed therein, and a knob or flange-like member 25 at one end thereof, as shown specifically in FIGS. 2 and 3 of the drawing.

The knob or member 25, as shown in the drawings, has a central aperture which is sized to facilitate passage therethrough with sufficient clearance of any obturator, scope and cutting element which is to be inserted into and withdrawn from the cannula 24 and which projects through longitudinal slot 26, as described in detail hereinbelow.

An obturator 28, as in FIGS. 6 and 7, is adapted to be slidably received within the cannula, and presents a smooth outer surface through the intermediary of an axial, upstanding rib portion 30 which is engageable in close conformance within the longitudinal slot of the cannula upon insertion therein. The leading end of the obturator 28 is a tapered tip portion 32 which is bent upwardly in a direction towards the longitudinal rib to impart to the tip a somewhat upward curvature for a purpose to be described hereinbelow in more extensive detail.

Although the cannula 24, as shown in FIGS. 2 and 3, is illustrated as being circular in cross-sectional configuration along its external surface, pursuant to a modified embodiment, as shown in FIGS. 4 and 5, at opposite sides of the longitudinal slot 26, the outer surface of the cannula 24 may be equipped with integrally formed outwardly extending curvilinear flange portions 36 and 38 so as to essentially form so-called wings or fins, as described further on hereinbelow. These fin-like wings or flange portions 36 and 38 are integrally formed with the cannula and are also curved so that upon insertion of the obturator into the cannula, the tip end of the obturator essentially forms a smooth curvature at its juncture with the flanges 36 and 38.

As shown more specifically in FIGS. 8 through 10, the endoscopic instrument 10 is illustrated in its condition for cutting through the flexor retinaculum to effectuate carpal tunnel or ligament release.

Hereby, the arthroscope 22 includes a suitable knurled knob 40 having an internal threaded portion 42 in a cylindrical extension 44 and a tapered bore 46 for receiving a tubular knife or cutting blade holder 48. The blade or knife holder 48 is adapted to receive a scope 50 of cylindrical configuration extending therethrough and lock the latter within the blade holder by simply axially displacing the knurled nut 40 through threaded interengagement between the internal thread 42 of the nut and an external thread 52 on the blade holder. This will cause the tapered bore 46 of nut 40 to either compress the slotted portion 54 of the blade holder to clampingly engage the scope 50 or to loosen it so as to enable axial adjustment thereof relative to the blade holder.

A scope in the form of a rod member, in the absence of a blade holder, and which is connected to a video scanner (not shown) is adapted to be inserted through the cannula for effective visualization of the operative site.

The scope 50, at the leading end thereof includes a mounting for a cutting element, such as a flat knife blade 60 having a leading cutting edge 62, and with the scope 50 having a tapered or angled forward end surface 64 enabling light to be projected against the cutting device so as to illuminate the region of the operating site.

The knife blade 60 is adapted to be slid through the cannula 24 while mounted on the scope 50, after being advanced through the member 25, and with the knife blade 60 being afforded sufficient clearance to be inserted into and withdrawn through the member 25, so as to be slidingly engaged within the longitudinal slot 26 of the cannula during the forward advance thereof and while severing the flexor retinaculum. Moreover, the extent of forward advance of the knife blade in the cannula is readily controlled by adjusting the relative axial positioning of the scope within the tubular blade holder 48 and thereafter clamping the scope within the knife holder through activation of the knurled knob 40.

As shown in FIGS. 11 and 12 of the drawings, the cutting blade 60 may also be directly mounted on the holder 48 for the cylindrical scope 50, which has the distal end thereof provided with the external thread 52 which is engageable with the clamping nut 40, and with the slotted end portion 54 adapted to be tightened onto the scope.

In order to ensure that the cannula 24 remains in the correctly inserted rotational position during the implementation of the endoscopic surgical procedures, the member 25 of the cannula 24 may be provided with one or more pins 70 of relatively short lengths and thin diameters, which extend in parallel axially spaced relationship with the body of the cannula. These pins 70, or pin 70, upon the insertion of the cannula into the incision will pierce the skin of the patient closely adjacent the incision and ensure that the cannula will not rotate so as to render certain that the slot 26 for receiving the cutting instrument 60 will always be in the proper relationship relative to the tissue which is to be severed thereby. Moreover, the member 25 may be provided with an internal radial slot extending coaxially with the longitudinal slot 26 in the cannula 24, and which is of a radial length so as to enable passage of the cutting member or knife 60 through the member 25 as the endoscopic element or scope 50 with the cutting member 60 mounted thereon, as shown in FIG. 11, is passed through member 25 into the cannula 24.

The inventive endoscopic surgical procedure for effecting carpal tunnel release utilizing the novel uniportal palmar subligmentous endoscopic carpal tunnel release technique, and employing the novel endoscopic surgical instrument 10 is now described hereinbelow, by way of example.

Initially, after the hand is prepped, a regional anesthesia is applied to the hand of the patient which is to be subjected to the operative procedure. Thereafter, two lines are drawn, one transversely across the palm from the distal border of the thumb and another between the middle and ring fingers of the patient. At the point of intersection of the lines, and at a proximity of 1 cm thereto, a 1.5 cm long incision is made in the thenar crease or in a slight ulnar direction. The incision is deepened to expose the palmar fascia through the intermediary of blunt scissors in order to avoid injury to the palmar cutaneous branch of the median nerve. The distal edge of the flexor retinaculum is identified and divided for 5 to 6 mm approximately. Throughout this process, the palmar arch and the median nerve branches are protected. This palmar fascia is then divided longitudinally exposing the flexor retinaculum.

The hand is thereafter placed on the hand rest or bolster 12, with the forearm to which a tourniquet has been applied being supported on the inclined surface 16. The wrist is hyperextended in that the hand is positioned palm facing upwardly on the curved surface 14 with the fingers depending forwardly, and then clamped by means of the strap 20 to the bolster.

In this hyperextended position of the hand, a curved dissector is inserted through the incision so as to cause the posterior surface of the flexor retinaculum to be carefully dissected so as to peel the synovial tissue off the flexor retinaculum. Suitable retractors maintain the incision in an open spread condition. This enables the open incision or wound to be thoroughly irrigated.

Thereafter, the curved dissector is withdrawn, and the cannula 24 with the obturator 28 positioned therein with its tip 32 forwardly extended, is advanced into the incision along the path previously defined by the dissector in close proximity to the internal surface of the flexor retinaculum. This closeness is enhanced by the curvature imparted to the tip of the obturator.

Thereafter the obturator 28 is withdrawn while permitting the cannula 24 to remain in place beneath the flexor retinaculum, and a scope (without a cutting blade) is inserted through the cannula 24 to enable thorough visualization of the posterior surface of the flexor retinaculum. Hereby, it is important to be able to identify the flexor retinaculum endoscopically through the presence of its transversely oriented fibers. In the event that the scope ascertains that there is a presence of some synovial tissue obstructing the visualization of the transverse fibers, either a blunt dissector or a blunt hook may be employed to peel the thin and generally flimsy synovial lining away from the flexor retinaculum. Alternatively, if this particular presence of such tissue is of a substantial nature, the cannula 24 is withdrawn, the obturator repositioned therein, and the entire procedure repeated. This must be implemented until such time as the transverse fibers of the flexor retinaculum are clearly viewed endoscopically.

Upon the transverse fibers of the flexor retinaculum being clearly identified, the scope is then withdrawn from the cannula 24, and the scope 50 having the cutting device, consisting of the blade 60 mounted thereon, is inserted through the cannula 24 and advanced towards the operating site represented by the transverse carpal ligament or flexor retinaculum. The angled leading end 64 of the scope 50 on which the cutting blade 60 is mounted enables projection of reilluminating light against the blade and the surrounding regions of the operating site so as to constantly afford direct unobstructed visualization of the operative region during the carpal ligament releasing procedure.

As the scope and the cutting device or blade 60 mounted thereon is advanced, the cutting edge 62 of the latter will divide the flexor retinaculum throughout its transverse width while being maintained under endoscopic visualization. Upon completion of the severing of the flexor retinaculum, the scope 50 and the thereon mounted cutting blade 60 are withdrawn from the cannula, and a scope without a cutting device thereon is reinserted into the cannula to provide for a viewing of the cut edges of the flexor retinaculum so as to ensure the complete division thereof has been accomplished. Once the intactness of the median nerve and surrounding structures have been verified through suitable rotation of the cannula about its longitudinal axis so as to afford a broader overview, the entire endoscopic surgical instrument 10 is withdrawn from the operating site out of the incision.

Prior to closing and suturing the incision, the wound is again inspected; on the one hand, by direct visualization of the cut edges of the flexor retinaculum, and on the other hand, by inserting the blunt dissector to assess the length and completeness of the division of the flexor retinaculum. The wound is then irrigated and sutured, with a tincture of benzoin applied thereto, thereafter applying a steristrip and the hand placed in a soft fluff dressing.

From the foregoing, it becomes readily apparent that the inventive surgical procedure, employing only a uniportal or single incision enables the operation to be implemented much more rapidly than heretofore, while forming only a cosmetically attractive small single scar in the palm, while extensively reducing the postoperative recovering period of the patients. In at least one-third of the patients, no pain was experienced postoperatively, obviating the necessity for any medication; in effect, one-third of the patients did not require medical care.

Moreover, the average length of time postoperatively for being able to gainfully utilize the hand and, thereby to return to work, was approximately 14 days, with executives normally being able to return to work at about 7 days subsequent to the operation, clerical/secretarial staff at approximately 17 days, and workers involved in heavy physical labor at approximately 28 days after surgery.

Although the foregoing description has been set forth with regard to the effectuation of carpal tunnel release, the present invention is also particularly directed to other surgical procedures, as follows:

a) Uniportal Plantar Fascia Release

After appropriate anesthesia, a line is drawn three inches distal to the medial malleous in the area which corresponds to a point that is anterior and distal to the plantar fascial insertion. Using a No. 15 blade, a 2 cm vertical incision is made into the soft tissue. Using a blunt dissector, a portion of the medial band of the plantar fascia is identified. Using a channeling device or a dissector, the inferior surface of the plantar fascia is channeled across the plantar fat to the lateral aspect of the foot. Next, the cannula-obturator assembly 24, 28 is introduced into the channel created, the obturator 28 is removed leaving the cannula 24 in place with the dorsal slot 26 of the cannula 24 looking up into the plantar fascia. Using a 4 mm endoscope, the scope 50 is inserted to identify the medial, central and lateral bands of the plantar fascia. The purpose is to release the medial band. Once it is made certain that the medial bands are exposed, the scope 50 is removed, and the knife-sleeve or scope combination 50, 60 is reintroduced into the cannula 24, and a division of the plantar fascia medial band is accomplished under endoscopic visualization. The surgeon may also choose to divide the central and lateral band in the same fashion. The scope-knife assembly 50, 60 is then removed from the cannula 24, and the knife is removed off the endoscope. Subsequently, the endoscope 50 is then reinserted into the cannula 24 to ascertain the division of the plantar fascia. Subsequently, the scope 50 is removed, the obturator 28 reintroduced into the cannula, and the removal of the obturator-cannula assembly 24, 28 is followed by wound closure, thus completing the plantar fascia release.

b) Release of Posterior Compartment of Leg for Compartment Syndrome

Under appropriate anesthesia, the patient is placed in the lateral decubitus position, following which the thigh is prepped and draped in the usual manner. A small transverse incision 1.5 to 2 cm is made to the medial aspect of the Achilles tendon through which the deep fascia of the leg is identified, and a small transverse incision is made in the deep fascia. A dissector is then introduced underneath the deep fascia to create a pathway for the introduction of the obturator and the cannula assembly 24, 28. This is carried as far as to the popliteal space following which the dissector is removed and the obturator and cannula assembly 24, 28 is introduced; the obturator 28 is then removed, and an endoscope 50 is introduced into the cannula 24 to totally visualize the fascia, assuring no other structure is seen. Subsequently, the scope 50 is removed, and the scope and the knife assembly 50, 60 is then placed in the cannula 24, and division of the fascia is accomplished under endoscopic visualization. The scope and knife assembly 50, 60 is then removed, following which the knife 60 is removed off the scope 50 and the scope reintroduced into the cannula 24 to confirm complete division of fascia. The scope 50 is then removed, the obturator 28 reintroduced into cannula 24 and obturator and cannula assembly 24, 28 conjointly removed. The wound is left open and dressed.

A similar procedure may be carried out for the other three compartments of the lower leg, (lateral compartment, anterior compartment, and deep posterior compartment) as well as the anterior and posterior compartments of the thigh.

c) Forearm Fascial Release for Fascial Compartment Syndrome

A 1.5 to 2 cm incision is made transversely across the distal crease of the wrist. Subsequently, the deep fascia of the forearm is exposed. Palmaris longus, if present, is retracted to the side, and subsequently a small transverse incision is made in the forearm fascia. After making the incision, a blunt dissector is introduced underneath the fascia to create a pathway for the introduction of the obturator and cannula assembly 24, 28. This dissector is then pushed further proximally underneath the deep fascia of the forearm until reaching the most proximal limits of the forearm fascia. After creating a pathway, the dissector is removed, followed by introduction of the obturator and cannula assembly 24, 28. Subsequently, the obturator 28 is removed and the cannula is left in place. The endoscope 50 is introduced into the cannula 24 to visualize the fascia of the forearm by the arrangement of its fibers making sure that no other structures are seen. Once this is done, the scope 50 is removed and special knife-sleeve or scope assembly 60 is slid over the scope 50 which is then introduced into the cannula 24 and under endoscopic visualization, complete division of the deep fascia of the forearm is accomplished. After this is completed, the scope and the knife assembly 50,60 is removed and the knife-sleeve assembly is removed off the scope 50 and the scope reintroduced into the cannula 24 to confirm complete division of the fascia. The procedure at this point is completed, the scope 50 is removed and obturator 28 is inserted into the cannula 24 and conjointly removed therewith. The incision at the wrist is left open. If at this point, there is a feeling that there is also present an associated compression on the median nerve, a carpal tunnel release can be performed in the manner as described hereinabove.

d) Lateral Release for Patella Realignment

The thigh is prepped and draped in the usual manner; subsequently, the appropriate anesthesia is administered. A 1.5 to 2 cm incision is transversely made in the area lateral to the patella and deepened to expose the fascia. The fascia is identified and then divided transversely 1 cm and thereafter a dissector introduced to separate the fascia from the underlying layers. Subsequently, the cannula and obturator assembly 24, 28 is introduced into the pathway created by the dissector. The obturator 28 is removed from the cannula 24 and a 4 mm endoscope 50 is introduced into the cannula 24 to completely visualize the fascia. The scope 50 is the removed from the cannula 24. The sleeve and knife assembly with the scope 50, 60 is introduced into the cannula 24. The lateral retinaculum is divided under endoscopic visualization for a distance of 4 to 6 inches. Subsequently, the knife and endoscope assembly 50, 60 is removed and the knife 60 removed from the scope 50, and the scope reintroduced into the cannula 24 for a total visualization of the division of the fascia. The scope 50 is then removed and the obturator 28 introduced into the cannula 24 and the obturator-cannula assembly is conjointly removed. The wound is then closed.

Quite apparently, by only slightly modifying the lengths and diameters of the inventive instrument, it is possible to customize, within the scope of the invention, the instrument so as to be adapted for numerous uniportal endoscopic surgical procedures of the type described and claimed herein.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A method of implementing a uniportal endoscopic surgical procedure to effectuate a plantar fascia release on the foot of a patient; comprising the steps of:

drawing a line distal to the medial malleous in an area which corresponds to a point which is anterior and distal to the plantar fascial insertion;

making an incision into the soft tissue on said patient at a locale proximate said operative site to establish an entry portal;

identifying a portion of the medial band of the plantar fascia and channeling the inferior surface of the plantar fascia across the plantar fat to the lateral aspect of the foot;

inserting an elongate insertion member into a longitudinal bore of an elongate cannular guide member having open proximal and distal ends and an open slot extending along the length thereof communicating with said open ends, said elongate insertion member being slidably receivable within said cannular guide member and being configured so that at least portions thereof conform with said open distal end and said open slot of the guide member to form a smooth exterior surface in combination therewith;

introducing a leading end of the combination of said cannular guide member and the therein inserted insertion member into said entry portal and advancing said combination a predetermined distance relative to said operative site;

withdrawing said insertion member while permitting said cannular guide member to remain in place at said operative site with the slot facing the plantar fascia;

inserting endoscopic viewing means into said cannular guide member for direct visualization of the medial, central and lateral bands of the plantar fascia and the positioning of said guide member relative to said site;

withdrawing said endoscopic viewing means from said cannular guide member;

mounting a surgical instrument on further endoscopic viewing means proximate the leading end of said further viewing means;

inserting said composite further endoscopic viewing means and surgical instrument into said cannular guide member such that the surgical instrument protrudes into the open slot in said cannular guide member, and advancing said composite endoscopic viewing means and surgical instrument so as to contact tissue at said operative site with said surgical instrument;

operatively engaging said tissue with said surgical instrument while advancing the latter under direct visualization through said further endoscopic viewing means so as to release at least the medial band of the plantar fascia;

withdrawing said composite further endoscopic viewing means and surgical instrument from said cannular guide member; and withdrawing said cannular guide member through said entry portal and suturing said incision.

2. A method as claimed in claim 1, wherein said surgical procedure includes selectively releasing the central and lateral bands of the plantar fascia.

3. A method of implementing a uniportal endoscopic surgical procedure on a patient to effectuate release of at least the posterior compartment of the leg; comprising the steps of:

making an incision on said patient transversely to the medial aspect of the Achilles tendon to identify the deep fascia of the leg and forming a small transverse incision in the deep fascia proximate said operative site to establish an entry portal;

forming a pathway beneath the deep fascia to the popliteal space;

inserting an elongate insertion member into a longitudinal bore of an elongate cannular guide member having open proximal and distal ends and an open slot extending along the length thereof communicating with said open ends, said elongate insertion member being slidably receivable within said cannular guide member and being configured so that at least portions thereof conform with said open distal end and said open slot of the guide member to form a smooth exterior surface in combination therewith;

introducing a leading end of the combination of said cannular guide member and the therein inserted insertion member into said entry portal and advancing said combination along said pathway a predetermined distance relative to said operative site;

withdrawing said insertion member while permitting said cannular guide member to remain in place at said operative site;

inserting endoscopic viewing means into said cannular guide member for direct visualization of said operative site and the positioning of said guide member relative to said site;

withdrawing said endoscopic viewing means from said cannular guide member;

mounting a surgical instrument on further endoscopic viewing means proximate the leading end of said viewing means;

inserting said composite further endoscopic viewing means and surgical instrument into said cannular guide member such that the surgical instrument protrudes into the open slot in said cannular guide member, and advancing said composite endoscopic viewing means and surgical instrument so as to contact tissue at said operative site with said surgical instrument;

operatively engaging said tissue with said surgical instrument while advancing the latter under direct visualization through said further endoscopic viewing means so as to perform a division of said fascia;

withdrawing said composite further endoscopic viewing means and surgical instrument from said cannular guide member;

withdrawing said cannular guide member through said entry portal and dressing said incision.

4. A method as claimed in claim 3, wherein said surgical procedure includes selectively dividing the fascia lateral compartment, anterior compartment and deep posterior of the leg, and the anterior and posterior compartments of the thigh.

5. A method of implementing a uniportal endoscopic surgical procedure to effectuate a forearm fascial release for fascial compartment syndrome on a patient; comprising the steps of:

making an incision on said patient transversely across the distal crease of the wrist to enable exposure of the deep fascia of the forearm proximate said operative site to establish an entry portal; retracting the palmaris longus and imparting a small transverse incision to the forearm fascia; and forming a pathway beneath the fascia to the proximal extent of the forearm fascia;

inserting an elongate insertion member into a longitudinal bore of an elongate cannular guide member having open proximal and distal ends and an open slot extending along the length thereof communicating with said open ends, said elongate insertion member being slidably receivable within said cannular guide member and being configured so that at least portions thereof conform with said open distal end and said open slot of the guide member to form a smooth exterior surface in combination therewith;

introducing a leading end of the combination of said cannular guide member and the therein inserted insertion member into said entry portal and advancing said combination along said pathway a predetermined distance relative to said operative site;

withdrawing said insertion member while permitting said cannular guide member to remain in place at said operative site;

inserting endoscopic viewing means into said cannular guide member for direct visualization of said operative site and the positioning of said guide member relative to said site;

withdrawing said endoscopic viewing means from said cannular guide member;

mounting a surgical instrument on further endoscopic viewing means proximate the leading end of said viewing means;

inserting said composite further endoscopic viewing means and surgical instrument into said cannular guide member such that the surgical instrument protrudes into the open slot in said cannular guide member, and advancing said composite endoscopic viewing means and surgical instrument so as to contact tissue at said operative site with said surgical instrument;

operatively engaging said tissue with said surgical instrument while advancing the latter under direct visualization through said further endoscopic viewing means so as to effectuate division of the deep fascia of the forearm;

withdrawing said composite further endoscopic viewing means and surgical instrument from said cannular guide member;

withdrawing said cannular guide member through said entry portal and dressing said incision.

6. A method as claimed in claim 5, wherein a carpal tunnel release is implemented in the presence of compression on the median nerve.

7. A method of implementing a uniportal endoscopic surgical procedure to effectuate a lateral release for patella realignment on a patient; comprising the steps of:

making an incision on said patient in a region lateral to the patella and exposing the fascia proximate said operative site to establish an entry portal; identifying and transversely dividing the fascia, and separating the fascia from underlying tissue to form a pathway;

inserting an elongate insertion member into a longitudinal bore of an elongate cannular guide member having open proximal and distal ends and an open slot extending along the length thereof communicating with said open ends, said elongate insertion member being slidably receivable within said cannular guide member and being configured so that at least portions thereof conform with said open distal end and said open slot of the guide member to form a smooth exterior surface in combination therewith;

introducing a leading end of the combination of said cannular guide member and the therein inserted insertion member into said entry portal and advancing said combination along said pathway a predetermined distance relative to said operative site;

withdrawing said insertion member while permitting said cannular guide member to remain in place at said operative site;

inserting endoscopic viewing means into said cannular guide member for direct visualization of said operative site and fascia and the positioning of said guide member relative to said site;

withdrawing said endoscopic viewing means from said cannular guide member;

mounting a surgical instrument on further endoscopic viewing means proximate the leading end of said viewing means;

inserting said composite further endoscopic viewing means and surgical instrument into said cannular guide member such that the surgical instrument protrudes into the open slot in said cannular guide member, and advancing said composite endoscopic viewing means and surgical instrument so as to contact tissue at said operative site with said surgical instrument;

operatively engaging said tissue with said surgical instrument while advancing the latter under direct visualization through said further endoscopic viewing means so as to divide the lateral retinaculum for a predetermined distance;

withdrawing said composite further endoscopic viewing means and surgical instrument from said cannular guide member;

withdrawing said cannular guide member through said entry portal and suturing said incision.

8. A method as claimed in any one of claims 1, 3, 5 or 7, wherein said insertion member comprises an obturator.

9. A method as claimed in claim 8, wherein said obturator has a tapered leading tip portion.

10. A method as claimed in claim 9, wherein said tapered leading tip portion of the obturator includes a curvature so as to angle the tip portion towards the plane of the cannular guide member possessing the open slot.

11. A method as claimed in any one of claims 1, 3, 5 or 7, wherein said surgical instrument comprises cutting means for severing tissue at said operative site.

12. A method as claimed in claim 9, wherein said cutting means comprises a blade member having a leading cutting edge for severing tissue responsive to advancing said further endoscopic viewing means forwardly within said cannular guide member.

13. A method as claimed in claim 10, wherein said open slot in said cannular guide member has the opposite said edges thereof forming guide surfaces for said blade member inhibiting rotation of said blade about the longitudinal axis of said cannular guide member.

14. A method as claimed in claim 10, wherein the leading end of said further endoscopic viewing means includes an angled surface facing said blade member for directing illuminating light against the blade member and towards the region of the operating site proximate at least the cutting edge of said blade member.

15. A method as claimed in any one of claims 1, 3, 5 or 7, wherein said first-mentioned endoscopic viewing means is reinserted into said cannular guide member after withdrawing said composite further endoscopic viewing means and surgical instrument to enable inspection of the operating site; withdrawing said endoscopic viewing means from said cannular guide member and reinserting said elongate insertion member into the bore of said cannular guide member whereby said cannular guide member is withdrawn through said entry portal conjointly with said insertion member.

16. A method as claimed in any one of claims 1, 3, 5 or 7, wherein means provide for adjustable limits in advancing said composite further viewing means and surgical instrument within said cannular guide member relative to said operative site.

\* \* \* \* \*